(12) United States Patent
Hirschfeld et al.

(10) Patent No.: US 10,314,637 B2
(45) Date of Patent: Jun. 11, 2019

(54) TRANSPORTER FOR CONTROLLING THE LONGITUDINAL MOVEMENT OF AN ELECTRODE

(71) Applicant: OLYMPUS WINTER & IBE GMBH, Hamburg (DE)

(72) Inventors: Simon Hirschfeld, Hamburg (DE); Harald Hanke, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 327 days.

(21) Appl. No.: 15/027,015

(22) PCT Filed: Dec. 17, 2014

(86) PCT No.: PCT/EP2014/003408
§ 371 (c)(1),
(2) Date: Apr. 4, 2016

(87) PCT Pub. No.: WO2015/090588
PCT Pub. Date: Jun. 25, 2015

(65) Prior Publication Data
US 2016/0235465 A1    Aug. 18, 2016

(30) Foreign Application Priority Data

Dec. 18, 2013 (DE) ........................ 10 2013 022 121

(51) Int. Cl.
*A61B 18/08* (2006.01)
*A61B 18/14* (2006.01)
*A61B 17/00* (2006.01)
*A61B 18/12* (2006.01)
*A61B 18/00* (2006.01)

(52) U.S. Cl.
CPC ...... *A61B 18/082* (2013.01); *A61B 17/00234* (2013.01); *A61B 18/12* (2013.01);
(Continued)

(58) Field of Classification Search
CPC ..... A61B 18/12; A61B 18/082; A61B 18/149; A61B 17/320016; A61B 17/2909;
(Continued)

(56) References Cited

U.S. PATENT DOCUMENTS 4,648,399 A    3/1987   Nakada
4,726,370 A *  2/1988   Karasawa ............. A61B 18/14
                                                    600/105
(Continued)

FOREIGN PATENT DOCUMENTS

DE           35 00 527 A1    7/1985

OTHER PUBLICATIONS

Jun. 21, 2016 International Preliminary Report on Patentability issued in International Patent Application No. PCT/EP2014/003408.
Mar. 10, 2015 International Search Report issued in International Patent Application No. PCT/EP2014/0034058.

*Primary Examiner* — Daniel W Fowler
*Assistant Examiner* — Katherine E Maziarski
(74) *Attorney, Agent, or Firm* — Oliff PLC

(57) ABSTRACT

A transporter for controlling the longitudinal movement of an electrode of a urological resectoscope, with a guide tube which is secured lengthwise on the resectoscope and on which a carriage is mounted so as to be longitudinally movable, with a spring mounted at one end on the carriage and at the other end on one of the ends of the guide tube, and with finger supports secured on the carriage and on one of the ends of the guide tube, is characterized in that the spring is formed in one piece with at least one of the finger supports, and wherein the spring is designed as a leaf spring and has portions curved in opposite directions.

7 Claims, 2 Drawing Sheets

Figure 1:
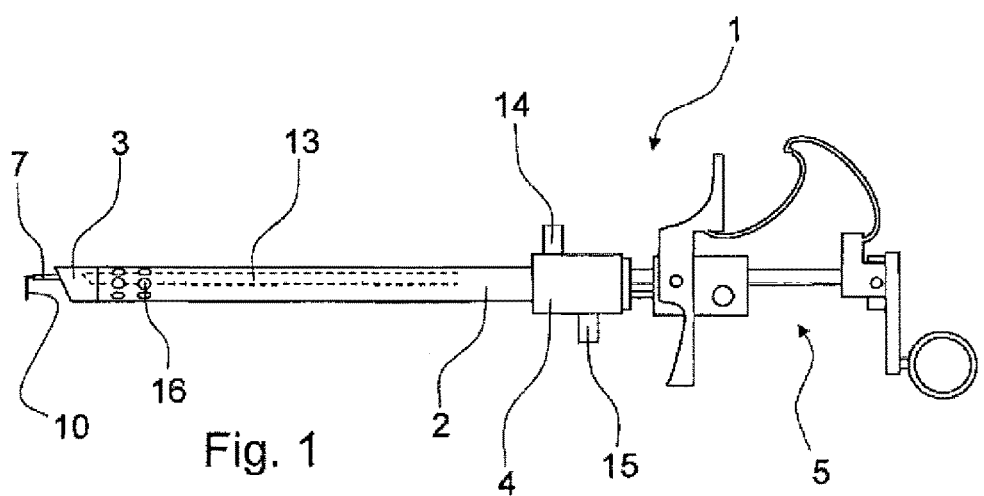

(52) U.S. Cl.
CPC .. *A61B 18/149* (2013.01); *A61B 2017/00274* (2013.01); *A61B 2018/00505* (2013.01); *A61B 2018/00547* (2013.01); *A61B 2018/00982* (2013.01)

(58) Field of Classification Search
CPC .......... A61B 2017/0042; A61B 17/282; A61B 2017/00234; A61B 2017/00367; A61B 2017/00862; A61B 2017/00991; A61B 17/00234; A61B 2018/00196; A61B 2018/1475
See application file for complete search history.

(56) References Cited

U.S. PATENT DOCUMENTS

| | | | |
|---|---|---|---|
| 5,556,376 A | 9/1996 | Yoon | |
| 5,843,017 A | 12/1998 | Yoon | |
| 6,358,200 B1 | 3/2002 | Grossi | |
| 7,101,370 B2 * | 9/2006 | Garito | A61B 17/2909 606/41 |
| 2003/0023258 A1 * | 1/2003 | DuMontelle | A61B 17/2909 606/184 |
| 2004/0242959 A1 | 12/2004 | Nosel | |
| 2008/0188711 A1 | 8/2008 | Eliachar et al. | |

* cited by examiner

TRANSPORTER FOR CONTROLLING THE LONGITUDINAL MOVEMENT OF AN ELECTRODE

The invention relates to a transporter of the type mentioned in the preamble of claim 1.

Resectoscopes of the generic type are used mainly in urology, where they are used primarily for the purpose of reducing the size of a hypertrophic prostate by resection of the urethra, that is, from the inside. However, resectoscopes can also be used in other surgical fields, such as for procedures in the uterus, for example.

Resectoscopes having transporters of the generic type constitute the standard construction in the prior art. They comprise a shaft tube in which an electrode carrier is arranged so as to be longitudinally movable, which can cut with an electrode in the area of the distal end of the shaft tube. In the process, the cut is usually made against the distal margin of the shaft tube. Commonly, the cut is made using a high-frequency current. Therefore, the distal end area of the shaft tube is normally configured to be insulating.

The electrode carrier is connected at its proximal end to the transporter by means of which it can be moved in the longitudinal direction in order to perform the cutting movement. The transporter is usually detachably fastened to the proximal end of the shaft tube, and comprises a carriage mounted so as to be longitudinally movable, by means of which the electrode carrier can be coupled for the shared longitudinal movement.

The actuation of the transporter usually occurs using the fingers of one hand, which on the one hand touch the carriage, and on the other hand touch the stationary portions of the transporter, which are firmly connected to the guide tube The movement of the transporter according to the prior art occurs against a resetting spring, which is usually configured as a leaf spring in the generic transporter. The spring is fastened with one end to the carriage and with the other end to the guide tube. Several possibilities exist, depending on whether an active or a passive transporter is needed, and whether the spring is to operate as a compression spring or as a tension spring.

The cut is usually made with a retraction movement of the electrode. In the case of the active transporter, the electrode is pulled back against the spring force (in the proximal direction). In the case of the passive transporter, the electrode is moved forward by hand and then released so that it is pulled back in a cutting movement by the spring force. The resetting spring is designed as a leaf spring according to the generic prior art.

Such prior art is disclosed, for example, in US 2004/0242959 A1, U.S. Pat. No. 6,358,200 or DE 35 00 527 A1.

In these constructions, the spring is not used for generating the resetting force applied to the electrode, but also uses the torsion-limiting property of the leaf spring to prevent twisting of this carriage, which, according to the prior art is usually mounted on a round guide tube which is present in the resectoscope for guiding the optic system.

Looking more closely at the generic constructions, one notices the use of a simple leaf spring which, however, has a surprisingly complicated construction. In each case the leaf spring is gripped at the ends, usually in a plastic block. This plastic block is hinged via an axial hinge to the carriage and to a stationary portion of the transporter, respectively. All this requires the use of various materials and complicated construction and manufacturing steps.

At the ends of the leaf spring there is [sic], as the known constructions show, in each case in the area in which finger rests are provided on the transporter. These are components which the operator touches with the fingers in order to operate the transporter. The proximal rest is usually configured as a finger ring. A finger rest for placing one or several fingers is provided distally. One commonly also finds two finger rests here that are provided above and beneath the guide tube. The finger rests have no other design functions, and are generally configured as plastic shells that are fastened to the carriage and components, respectively, which are situated at one end of the guide tube. The finger rests are thus situated where the spring also engages, as a result of which the construction becomes more complicated.

U.S. Pat. No. 5,843,017 A discloses a medical instrument with a transporter, in which a carriage is longitudinally movable by compression of a U-shaped handle. It is proposed to arrange a leaf spring for spring preloading of the carriage in the housing of the instrument, coaxially around a guide tube and distally with respect to the handle.

The object of the invention is to provide a generic transporter that has a simpler and more cost effective construction.

This object is achieved with the features of the characterizing portion of claim 1.

According to the invention, the spring is configured to form a single piece with at least one of the finger rests, preferably with all the finger rests according to claim 2. According to claim 3, the integrated component thus produced is made entirely of spring-resilient plastic that has sufficient properties for the spring purposes.

The result is a single-piece construction which, in the affected construction area, replaces, as a single piece, the essential elements engaging there, that is, in particular the spring and the finger rests. This causes no problems in tennis of material technology. The construction can be made from metal or preferably from plastic. Plastics with appropriate spring properties are commercially available and also have the strength values required for the finger rests.

The manufacturing of the transporter is considerably simplified by the construction element provided by the invention. The construction element, of which there is now only one in this area, is connected at the two ends to the transporter by a screw connection or other connection possibilities. All other mounting steps required heretofore, such as in particular the premounting of the spring comprising multiple parts, the separate mounting of the spring and the finger rests, and the like are dispensed with. The result is a considerable saving effect. In addition, the invention provides a single-piece component, which in comparison to multipart components has the advantage of being gap-free and thus easier to clean.

Additional saving possibilities exist due to the single-piece manufacture of a relatively complex component. The entire component can be injected-molded from plastic, for example, so that significant saving effects result, even in medium-size series.

The construction according to the invention also allows deviations from the U-shaped configuration of the leaf spring, which was always preferred in the past for manufacturing reasons. In the case of manufacture by injection molding, or, for example, by cutting out or stamping from a plate, springs having shapes of any degree of complexity can be used at low cost. Thus, in particular, the embodiment according to claim 4 can be used, wherein the spring comprises sections bent in opposite directions. As a result, the course of the spring force over the path can be optimized. For example, the spring can be configured in the shape of an S in some sections, wherein two sections of the S-shaped spring area in each case are bent in opposite directions. A first bulge of the S shape is bent in a first direction, and a second bulge of the S shape is bent in a second, opposite direction. A spring area can also have a C-shaped configuration, for example wherein the end sections of the C-shaped spring area are bent in opposite directions.

Figure 2:
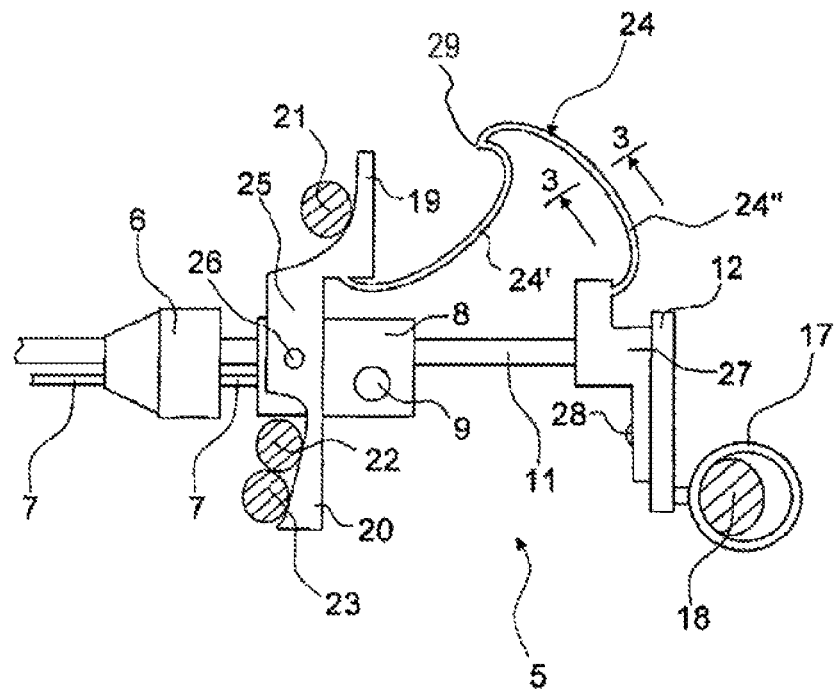
Figure 3:
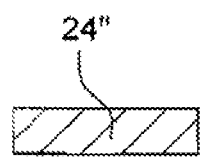

The invention is schematically illustrated in the drawings as an example. The figures show:

FIG. 1 a side view of a resectoscope with the transporter according to the invention, FIG. 2 an enlarged view of the transporter of FIG. 1, and FIG. 3 an enlarged section along line 3-3 in FIG. 2.

FIG. 1 shows, in a side view, a urological resectoscope 1 with a shaft tube 2 which in the usual configuration is made of metal, but which in its distal end area 3 is made of an insulator, for example ceramic. At the proximal end of the shaft tube 2, there is an end body 4 which is configured as a detachable coupling piece, using means that are not shown.

A transporter 5, which is illustrated in an enlargement in FIG. 2, can be coupled to the end body 4.

FIG. 2 shows a coupling part 6 of the transporter 5, which for the coupling fastening is insertable into the end body 4.

An electrode carrier 7 extends through the shaft tube 2, and extends through the coupling piece 6 so as to be longitudinally movable and fastenable in a carriage 8 of the transporter 5 by means of a locking button 9. The electrode carrier 7 can be moved in the longitudinal direction of the shaft tube 2 by longitudinal movement of the carriage 8. In this way, an electrode 10 arranged at the distal end of the electrode carrier 7 can be adjusted longitudinally, the electrode usually being configured in the shape of a U.

The carriage 8 is mounted, so as to be longitudinally movable in the direction of the shaft tube 2, on a guide tube 11 which passes through the coupling piece 6 and is fastened thereto.

The guide tube 11 is fastened to an end plate 12 at the proximal end. The carriage 8 can be moved on the guide tube 11 from the distal stop on the coupling piece 6 to the proximal stop on the end plate 12.

As a result, the electrode 10 can be longitudinally adjusted in the area of the distal end of the shaft tube 2. The construction is usually configured in such a manner that the electrode 10 cuts against the lower area of the distal margin of the end area 3. All this occurs within the viewing area of an optic system 13, shown only in broken lines in FIG. 1, which can be inserted from the proximal end of the transporter 5 through the guide tube 11 into the work position illustrated.

By means of the illustrated resectoscope 1, it is possible in particular to cut off tissue in the prostate in fairly large, flat pieces. Bleeding that occurs in the process, causing impediments to vision, is controlled in the usual way by rinsing with a clear rinsing fluid. To accomplish this, the illustrated resectoscope 1 uses the usual continuous permanent rinsing. Rinsing fluid is led into and out of the shaft tube 2 at connections 14 and 15. In the interior, the shaft tube 2 is subdivided into two channels, for example, by means of a dual tube system. One of the channels runs rinsing fluid through the distal opening of the shaft tube 2, while the other channel allows rinsing fluid to flow out of lateral openings 16 of the shaft tube 2.

Working with such a resectoscope 1 requires the utmost manual skill and continuous mental alertness in overviewing the complicated surgical area located inside the prostate, which is closed off from the outside and which the surgeon must envision in three dimensions in order to be able to work in it, pushing and rotating in all directions in a controlled manner.

For this purpose, particularly exact and finely sensitive operability of the transporter 5 is required. From the transporter, it must be possible to control the electrode 10 with utmost precision in all directions in all the movement sequences.

In the usual technique with a resectoscope 1 of the illustrated design, a drawing cut is made. For cutting, the electrode 10 is pulled back in the proximal direction. Shortly beforehand, the cutting voltage is applied to the electrode 10, which for this purpose is connected via the electrode carrier 7 and the carriage 8 and beyond same to a high-frequency generator with a switch configured as a foot switch, for example.

To make a cut at a certain site and in a certain rotation position, the resectoscope 1 is moved to the site of the cut with the electrode 10 distally extended. The voltage is then switched on and the carriage 8 is subsequently pulled back in the proximal direction. The voltage is then switched off and the electrode is moved back into the initial position.

In the construction represented in FIG. 1, the retracting movement of the electrode 10 used for cutting is generated by hand by touching with the fingers of one hand the carriage 8 on the one hand, and the end plate 12 on the other hand. Finger rests are situated at the corresponding sites in order to improve the sensitive operability.

As shown in FIG. 2, the finger rests are a finger ring 17 which is attached to the end plate 12 and into which the operator sticks his/her thumb 18. An upper finger rest 19 and a lower finger rest 20 are fastened to the carriage 8. In the process, the upper finger rest 19 is used for resting the index finger 21, and the lower finger rest 20 is used for resting the middle finger 22 and the ring finger 23. As can be seen in FIG. 2, the upper and the lower finger rests can each be configured as a web. As provided in this exemplary embodiment, the finger rests 19, 20 in each case can comprise a distal front side with a contact area for resting the fingers, and a rear side facing the contact area and not in contact with the fingers.

In the construction according to the invention illustrated in FIG. 1 and in particular in FIG. 2, the retracting movement of the carriage 8 used for the cutting occurs against a spring 24 which braces the carriage with respect to the end plate 12. This ensures that after the retracting cutting movement, the carriage 8 with the electrode 7 is again moved automatically in the distal direction back into the starting position.

A so-called active transporter is involved here. However, in some countries the passive transporter is preferred. In the case of the passive transporter, the spring could be arranged exactly as in FIG. 2. However, it would be used as a tension spring. The finger ring 17 would then be situated on the carriage 8, and the finger rests 19 and 20 would be situated on the coupling piece 6. Due to the finger action, the carriage 8 would thus be moved in the distal direction and then automatically returned under the action of the spring, in the process of which the cut is made.

FIG. 2 shows an active transporter with a spring 24 to which pressure is applied. A tension spring could also be used, which would then have to be arranged between the carriage 8 and the coupling piece 6.

As is also known from the prior art, the spring 24 is configured as a leaf spring, shown in cross section in FIG. 3. In the prior art, such a leaf spring would be coupled to end pieces, which could also be made of other materials, wherein the leaf spring is usually made of metal. The finger rests 17, 19 and 20 would have to be mounted separately.

In the present invention, the spring 24 is formed as a single piece with the distal finger rests 19 and 20, wherein the distal finger rests 19 and 20 have a continuous design with a middle part 25, which is fastened to the carriage 8 via a fastening means 26, for example, a screw. As can be seen in FIG. 2, it is provided that the spring 24 is connected to the finger rest in the back area thereof. This prevents inadvertent touching of the spring 24 or a portion of the spring 24 when the carriage 8 is moved due to finger pressure. As a result, complex spring shapes can be used, wherein the spring mechanism or the spring action achieved by the spring mechanism is protected against undesired influence due to contact with the fingers. It is particularly advantageously conceivable to arrange the spring 24 vertically—viewed in the transverse direction with respect to the guide tube 11—between the guide tube 11 and the contact areas provided for the fingers, so that the spring 24 engages vertically between the fingers and the guide tube 11. This ensures a good spring action of the transporter and promotes particularly smooth movement of the carriage 8.

At the other end of the spring 24, the spring is also designed in a single piece with an end piece 27 that is fastened to the end plate 12 via a fastening means 28. The spring 24 together with the proximal end piece 27 and the parts 19, 20 and 25 fastened to the carriage 8 are designed as a single piece. This complex component can be injection-molded from plastic, for example, or stamped or cut out from a plate of appropriate thickness, for example by means of a laser. The material must have appropriate spring properties and sufficient strength.

The spring 24 can have a U shape, for example, as in the prior art; however, according to FIG. 2, it is advantageously configured with the curved sections 24' and 24" which in each case comprise sections bent in opposite directions. For example, it is possible to provide that the end areas of a curved section 24', 24" are not oriented parallel, as in a U shape, but instead point in opposite directions. For example, as indicated particularly in FIG. 2, the curved sections 24' and 24" can be curved in the shape of a C. The end areas of the C shape point in opposite directions.

An S-shaped course of a curved section 24', 24" (not shown) is also conceivable, wherein, for example, the end areas of a curved section 24', 24" extending in the shape of an S point in opposite directions. Alternatively or in addition to the end sections of the curved sections 24', 24", other sections can also have opposite bends. For example, in an S shape—relative to a direction—a convex and a concave curvature are provided which form two sections that are bent in opposite directions.

As indicated in FIG. 2, the curved sections 24', 24" can form spring legs of the spring 24. It is also conceivable for at least one spring leg of the spring 24 to comprise multiple curved sections 24', 24". In addition, it is conceivable for some of the curved sections 24', 24" to be arranged parallel to one another or at a substantially constant distance from one another.

In the exemplary embodiment according to FIG. 2, it has been considered that the bent sections 24' and 24" are configured in each case with one of their end areas converging to a tip relative to one another. The two curved sections 24' and 24" thus transition into one another at a tip 29 in this exemplary embodiment. The result is a geometrically highly complex shape that has advantageous bending properties, in particular to ensure a suitable force progression over the movement range of the carriage 8.

In the embodiment represented in FIG. 2, the finger ring 17 is not formed as a single piece with the spring 24, and can be made of metal, for example, while the spring 24 is made of plastic.

In the proximal end area, the spring 24 is formed as a single piece with the end piece 27. In an alternative design, this end piece can be formed as a single piece with the end plate 12, which then can also be formed as a single piece with the finger ring 17. The principle of the invention can be advantageously expanded in this way.

| List of reference numbers | |
| --- | --- |
| 1 | Resectoscope |
| 2 | Shaft tube |
| 3 | Distal end area |
| 4 | End body |
| 5 | Transporter |
| 6 | Coupling piece |
| 7 | Electrode carrier |
| 8 | Carriage |
| 9 | Locking button |
| 10 | Electrode |
| 11 | Guide tube |
| 12 | End plate |
| 13 | Optic system |
| 14, 15 | Connections |
| 16 | Openings |
| 17 | Finger ring |
| 18 | Thumb |
| 19 | Upper finger rest |
| 20 | Lower finger rest |
| 21 | Index finger |
| 22 | Middle finger |
| 23 | Ring finger |
| 24 | Spring |
| 24', 24" | Curved sections |
| 25 | Middle part |
| 26 | Fastening means |
| 27 | End piece |
| 28 | Fastening means |
| 29 | Tip |

The invention claimed is:

1. A transporter for controlling longitudinal movement of an electrode of a urological resectoscope, comprising:
    a guide tube that is fastened lengthwise to the resectoscope;
    a carriage being mounted on the guide tube such that the carriage moves in a longitudinal direction;
    a spring that includes a first end and a second end, the first end being fastened to the carriage and the second end being fastened to the guide tube; and
    a first finger rest that is fastened to the carriage and a second finger rest that is fastened to one end of the guide tube, wherein:
    the spring is formed as a single piece with at least one of first finger rest and the second finger rest;
    the spring is a leaf spring having a first curved section and a second curved section, the first curved section and the second curved section curving in opposite directions; and
    the first curved section and the second curved section converge at an acute angle to form a pointed shaped structure.

2. The transporter according to claim 1, wherein the first finger rest comprises an upper finger rest and a lower finger rest, the spring is formed as a single piece with the upper finger rest and the lower finger rest.

3. The transporter according to claim 1, wherein the spring is formed as a single piece with the first finger rest and the second finger rest.

4. The transporter according to claim 1, wherein the spring, the first finger rest, and the second finger rest are formed from a spring-resilient plastic.

5. The transporter according to claim 1, wherein the first curved section and the second curved section are C-shaped or S-shaped.

6. The transporter according to claim 1, wherein the spring is connected to at least one of the first finger rest and the second finger rest on a rear side relative to a contact area of the finger rest.

7. The transporter according to claim 1, wherein the spring is arranged vertically between a contact area provided for the fingers and the second finger rest that is fastened to the guide tube.

* * * * *